US009297792B2

(12) United States Patent
Hotier

(10) Patent No.: US 9,297,792 B2
(45) Date of Patent: Mar. 29, 2016

(54) ANALYSIS DEVICE AND ASSOCIATED METHOD FOR OPERATING SIMULATED MOVING BED XYLENES SEPARATION UNITS A RAMAN SPECTROMETER

(71) Applicant: AXENS, Rueil-Malmaison (FR)

(72) Inventor: Gerard Hotier, Rueil-Malmaison (FR)

(73) Assignee: AXENS, Rueil-Malmaison (FR)

( * ) Notice: Subject to any disclaimer, the term of this patent is extended or adjusted under 35 U.S.C. 154(b) by 72 days.

(21) Appl. No.: 14/302,526

(22) Filed: Jun. 12, 2014

(65) Prior Publication Data

US 2014/0368810 A1    Dec. 18, 2014

(30) Foreign Application Priority Data

Jun. 14, 2013   (FR) ...................................... 13 55516

(51) Int. Cl.
| | |
|---|---|
| G01N 21/00 | (2006.01) |
| G01N 33/24 | (2006.01) |
| C07C 7/12 | (2006.01) |
| G01N 21/65 | (2006.01) |
| G01K 7/02 | (2006.01) |
| B01D 15/18 | (2006.01) |
| G01N 21/84 | (2006.01) |

(52) U.S. Cl.
CPC .......... *G01N 33/241* (2013.01); *B01D 15/1842* (2013.01); *C07C 7/12* (2013.01); *G01K 7/02* (2013.01); *G01N 21/65* (2013.01); *G01N 2021/8416* (2013.01)

(58) Field of Classification Search
CPC ... H01J 37/32935; G01N 21/64; G01N 21/65; G01N 21/68; G01N 2015/1037; G01J 3/02; G01J 3/44
USPC ....................................... 356/72–73, 300–445
See application file for complete search history.

(56) References Cited

U.S. PATENT DOCUMENTS

| 8,194,245 B2 | 6/2012 | Hotier et al. |
|---|---|---|
| 2011/0198500 A1 | 8/2011 | Hotier et al. |
| 2013/0053610 A1 | 2/2013 | Leinekugel Le Cocq et al. |
| 2013/0158332 A1* | 6/2013 | Rauch ................... G01J 3/4412 585/821 |

OTHER PUBLICATIONS

Search Report for FR1355516 dated Mar. 11, 2014.
Marteau, Philippe et al., "Remote Raman spectroscopy for process control," Vibrational Spectroscopy, 1995, vol. 9, pp. 101-109.

* cited by examiner

*Primary Examiner* — Abdullahi Nur
(74) *Attorney, Agent, or Firm* — Millen, White, Zelano, Branigan, P.C.

(57) ABSTRACT

The present invention describes an analysis device and a method associated with this device, said device comprising an analysis cell (8) containing an optrode (10), receiving an input laser signal and sending an output signal to the Raman spectrometer, and said method using two analysis routes: an analysis route 1 connected to the internal circulation current passing from adsorber B to adsorber A, and an analysis route 2 connected to the distilled raffinate originating from distillation column C.

9 Claims, 2 Drawing Sheets

ANALYSIS DEVICE AND ASSOCIATED METHOD FOR OPERATING SIMULATED MOVING BED XYLENES SEPARATION UNITS A RAMAN SPECTROMETER

FIELD OF THE INVENTION

The present invention relates to the field of on-line measurement methods and devices for the monitoring and regulation of simulated moving bed (abbreviated to SMB) xylenes separation units or distillation separation units.

More precisely, the present invention relates to the on-line measurement of the compositions of hydrocarbon streams circulating in the various separation zones of said units. This measurement of the concentrations is obtained from the Raman spectra of the stream in question, by a specific method for processing said spectra which forms an integral part of the present invention.

An instance of a particularly useful application of the method according to the present invention is the separation of the various xylenes, the streams circulating in the unit being constituted by a mixture of meta-xylene, ortho-xylene, para-xylene and ethylbenzene of variable composition depending on the measuring point in the separation unit considered.

EXAMINATION OF THE PRIOR ART

The Applicant's U.S. Pat. No. 5,569,808 describes an analysis method and device comprising a combination of:
one or more laser-emitting sources (visible or near-infrared),
at least 2 emitting optical fibres conveying said signal to two points within the unit,
para-xylene separation,
at least two optrodes capable of collecting the Raman signal backscattered by 2 samples,
representative of the streams circulating in the unit and eliminating parasitic signals,
at least 2 optical fibres conveying the signals collected by the optrodes to a
spectrometer comprising a detector comprising several analysis ranges.

The analysis method consists of measuring the spectrum re-emitted in a very particular wavelength range in which each of the six constituents toluene, ethylbenzene, para-, meta- and ortho-xylene and para-diethylbenzene displays an individual peak clearly distinct from those of the other 5 constituents.

Document U.S. Pat. No. 8,194,245 refines the analysis method by specifying in particular how to improve the accuracy of the analysis by taking into account the temperature of the sample and how to eliminate the fluorescence from certain compounds present in the form of traces by using one or more laser sources emitting at 785 nm.

Reference may also be made to the patents U.S. Pat. No. 7,116,414 and U.S. Pat. No. 7,548,310 which describe RAMAN sampling and analysis in a manner very far from that of the present invention.

Document US 2013/0053610 A1 describes a xylenes separation process using two adsorption columns connected in series.

For analysis route 1 (AR1):
liquid sent from adsorber B to adsorber A (called internal current recirculation from the bottom of adsorber B to the top of adsorber A),
extract originating from one or other of the adsorbers,
raffinate originating from one or other of the adsorbers.

For analysis route 2 (AR2):
distilled raffinate originating from distillation column C,
feed of the unit at the inlet of one or other of the adsorbers,
liquid sent from adsorber A to adsorber B (called internal current recirculation,
from the bottom of adsorber A to the top of adsorber B).

Figure 1:
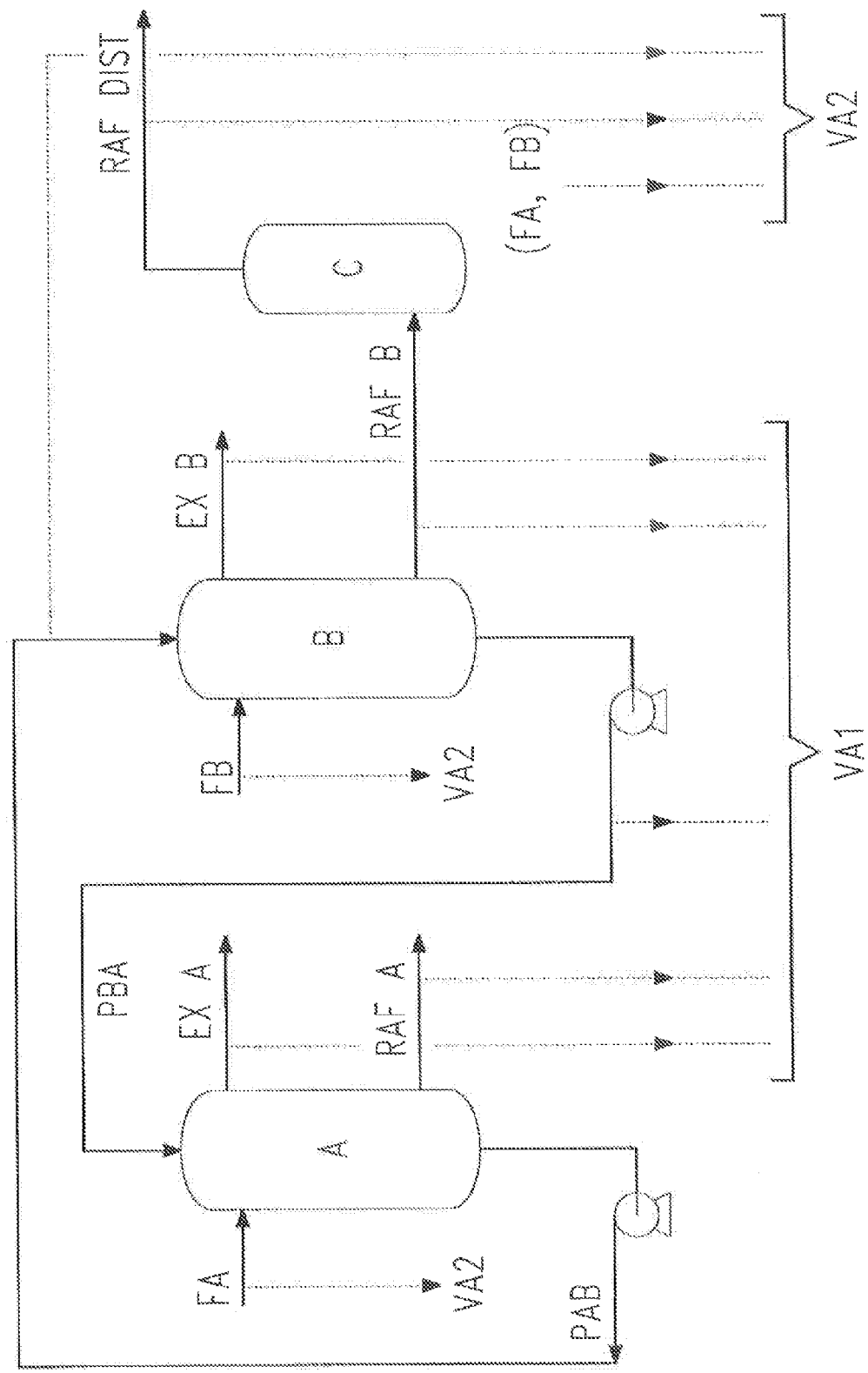
FIG. 1 describes a separation process in a simulated moving bed comprising two adsorbers A and B and the different sampling points which can be used according to the invention. These sampling points are the following.
Figure 2:
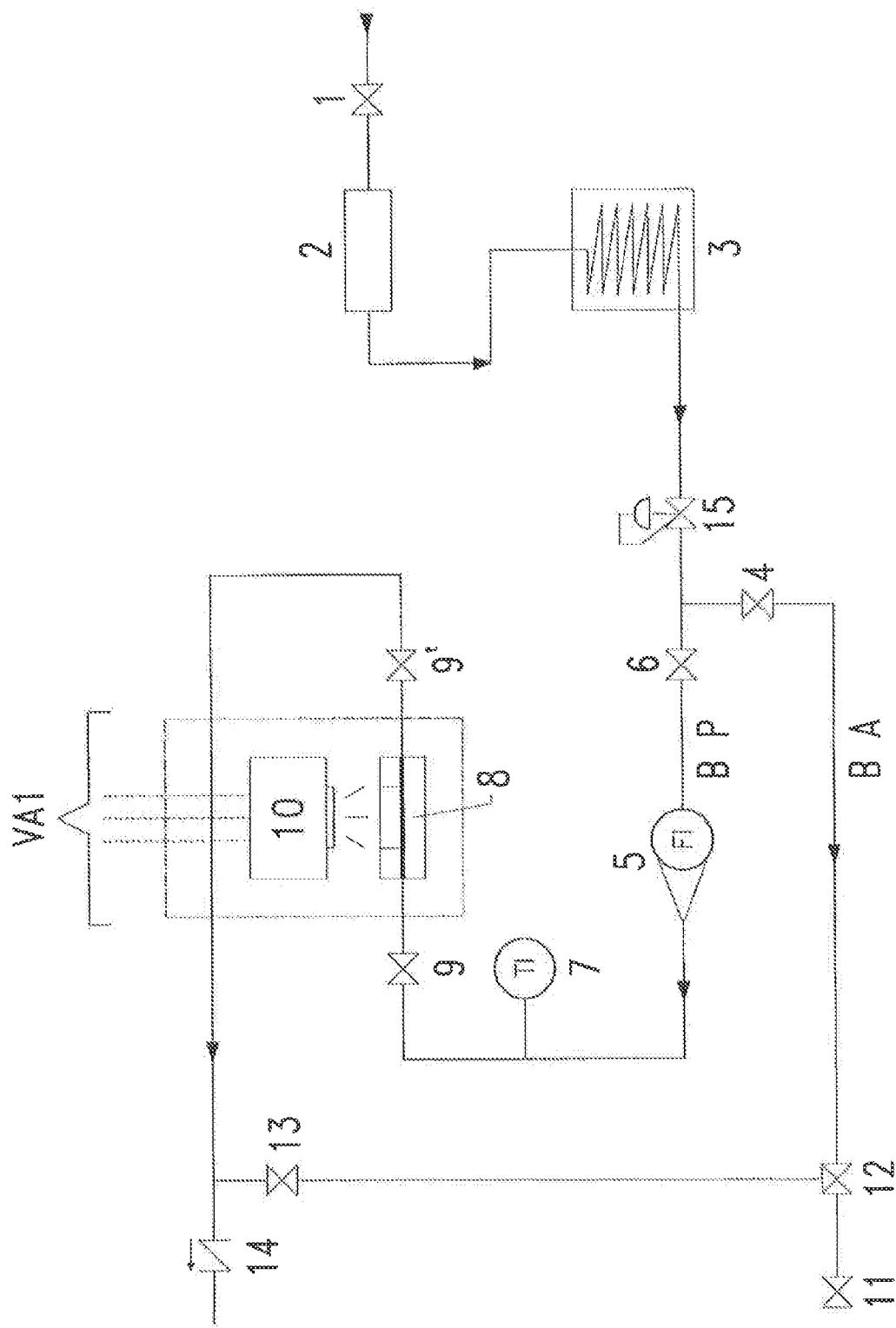

FIG. 2 details the sequence of the equipment encountered following an analysis route along the main branch intended for collecting samples for Raman analysis. As both analysis routes have the same equipment, only route AR1 is shown.

BRIEF DESCRIPTION OF THE INVENTION

The present invention can be defined as a device for measuring concentration by analyzing a Raman spectrum relating to sampling points of a simulated moving bed xylenes separation unit (called an SMB unit). The use of such Raman spectra for arriving at a measurement of the concentrations of the species present in the unit is known from the prior art and in particular the methodology of passing from the raw spectrum to the concentrations by a matrix inversion method described in the document U.S. Pat. No. 8,194,245.

The present device preferentially applies to a xylenes separation unit using two adsorbers A and B connected in series, i.e. with the circulation current originating from the bottom of adsorber A sent to the top of adsorber B, and with the circulation current originating from the bottom of adsorber B sent to the top of adsorber A.

More precisely, we shall hereafter refer to the invention as a simulated moving bed (called an SMB) xylenes separation unit, using two adsorbers A and B connected in series as previously, said unit comprising a device for measuring concentration by analyzing a Raman spectrum relating to sampling points, said device being constituted by two identical and independent routes.

The device according to the present invention is therefore constituted by two identical and independent analysis routes, called route 1 and route 2, each route having two branches, one called the "main branch" operating for the majority of the time, the other called the "subsidiary branch" operating for a very minority part of the time (i.e. a proportion of time less than 1% of the total operating period).

The points for collecting the samples to be analyzed are defined as follows:
for analysis route 1 (AR1):
  a) internal circulation current sent from adsorber B to adsorber A,
  b) extract originating from one or other of the adsorbers,
  c) raffinate originating from one or the other of the adsorbers.

for analysis route 2 (AR2):
  d) distilled raffinate (leaving distillation column C),
  e) feed of the unit at the inlet of one or other of the adsorbers,
  f) internal circulation current from adsorber A to adsorber B.

Each analysis route (AR1) or (AR2) comprises the following series of components taken in the direction of the stream to be analyzed (FIG. 2):

- a shut-off valve (1),
- a filter body (2) into which is inserted a filtering strainer with a cut-off threshold comprised between 3 and 15 microns and preferentially comprised between 5 and 7 micrometres,
- an exchanger (3) in which the hydrocarbon circulates on the tube side and cooling water on the shell side, the exchanger comprising on the shell side a circulation of cooling water at a temperature comprised between 5° C. and 40° C., and on the tube side a circulation of hydrocarbons, the inlet temperature of which is comprised between 135° C. and 175° C. and the outlet temperature between 20° C. and 60° C.,
- a pressure regulator (15) making it possible to regulate the downstream pressure and a pressure measurement means such that, based on an upstream pressure comprised between 0.9 and 1.6 MPa, a constant downstream pressure comprised between 0.2 and 0.5 MPa is obtained.

Each analysis route comprises two distinct branches with mutually exclusive operation, branch 1, called the "main" branch (denoted MB) being used for the Raman analysis and branch 2 called the "subsidiary" branch (denoted SB) being used for collecting samples for analysis purposes, in order to calibrate and/or optionally recalibrate the values obtained from the Raman measurement.

Branch 1 of each analysis route comprises the following main components taken in the direction of the stream to be analyzed:

- a shut-off valve (6) making it possible to force the circulation into branch 2 in certain situations,
- a thermocouple (7) making it possible to take the temperature of the sample to be analyzed,
- an analysis cell (8) containing an optrode (10), receiving an input laser signal and sending an output signal to the Raman spectrometer, the internal volume of said analysis cell (8) being of the order of 1 cm$^3$,
- a second set of shut-off valves (9, 9') for isolating the analysis cell (8) in the event of maintenance.

According to a variant of the present invention, the device for measuring concentration by analyzing a Raman spectrum is such that the analysis cell (8) and the optrode (10) are contained in the same containment cell.

According to another variant of the device for measuring concentration by analyzing a Raman spectrum according to the invention, the volume of hydrocarbon to be analyzed contained in the analysis cell (8) is renewed between 2 and 25 times per second.

According to another variant of the device for measuring concentration by analyzing a Raman spectrum according to the invention, the optrode (10) is linked to an input optical fibre providing a laser signal with a wavelength comprised between 400 nm and 1080 nm, and preferentially comprised between 520 nm and 785 nm (nm being the abbreviation for nanometre, i.e. $10^{-9}$ m).

The present invention also relates to a method for use of the previous device, said method using the two analysis routes 1 and 2 which are for the majority of the time connected as follows:

analysis route 1 is connected to the internal circulation current passing from adsorber B to adsorber A,
analysis route 2 is connected to the distilled raffinate originating from distillation column C.

According to a variant of the method according to the invention, for the minority of the time corresponding to transitional situations, analysis route 2 is connected to the feed injected into one or the other of the adsorbers.

According to another variant of the method according to the invention, in the event of maintenance on analysis route 1 (AR1), analysis route 2 (AR2) is connected to the internal circulation current from adsorber A to adsorber B.

According to another variant of the method for analyzing the concentrations according to the invention, the total volume of the circuit between the sampling point and the measuring point is such that the circulation time between said points is comprised between 1 and 75 seconds, the linear speed in the analysis cell (8) being comprised between 0.08 and 0.12 m/s.

According to another variant of the method for analyzing the concentrations according to the invention, the components of the device are calculated in order to ensure the following combination of operating conditions in the analysis cell (8):

1) sample substantially free of solid particles in suspension (i.e. containing less than 10 ppb, ppb meaning parts per billion)
2) sample the temperature of which is comprised between 20° C. and 60° C.
3) sample the pressure of which is comprised between 0.2 and 0.5 MPa (1 MPa=$10^6$ Pa)
4) linear speed comprised between 0.02 and 0.25 m/s and preferably between 0.05 and 0.2 m/s, and very preferably between 0.08 and 0.15 m/s.

According to another variant of the method for analyzing the concentrations according to the present invention, in the event of the simulated moving bed unit operating in degraded mode, the sampling line is disconnected from the first analysis route (AR1) in order to connect it to one of the following points:

Extract leaving adsorber A or B (according to whether A or B is operating in degraded mode), just upstream of the extract control valve, the pressure-temperature pair being chosen as follows: pressure variable from 0.9 to 1.4 MPa (MPa=$10^6$ Pa), temperature within the range of from 150° C. to 185° C., Raffinate leaving adsorber A or B (according to whether A or B is operating in degraded mode): just upstream of the raffinate control valve, the pressure-temperature pair being chosen as follows: pressure variable from 0.9 to 1.4 MPa, temperature comprised between 150° C. and 185° C., According to another variant of the method for analyzing the concentrations according to the present invention, the second analysis route (AR2) is applied at one of the following sampling points:

Distilled raffinate: located at the discharge of the feed pump of the isomerization unit, temperature comprised between 120° C. and 160° C., pressure comprised between 1 and 1.6 MPa, Feed: located between the feed pump discharge and the feed control valve, temperature comprised between 150° C. and 185° C., pressure comprised between 1.6 and 2 MPa, Recirculation liquid sent from the bottom of adsorber A to the top of adsorber B: temperature comprised between 0° and 80° C., pressure comprised between 0.15 and 0.5 MPa.

The present invention also relates to a sampling method coordinated with the operation of the unit in an SMB, capable of delivering as many samples (N) as there are beds (N) in a simulated moving bed (SMB) separation unit, the collecting of each of the samples N being commenced at points in time t1, t2, t3 ... tN linked to each other by the relationships:

$$t2 = t1 + T/N$$

$$t3 = t2 + T/N$$

T denoting the cycle time of the separation process in an SMB, i.e. the time at the end of which the positions of the injection and draw-off points have returned to their initial position, and t1 being an arbitrary time chosen within the range 5, (T/N)–5 expressed in seconds (the FIG. 5 therefore has the physical meaning of 5 seconds and is consistent with T also expressed in seconds), and each sampling period θ being comprised between 0.5 and 50 seconds, and preferentially comprised between 2 and 20 seconds.

Preferably, said sampling method is implemented with the device according to the invention.

Finally the present invention also relates to a method for calibrating (or recalibrating) the Raman spectrometer in conjunction with the sampling method, characterized by the following stages:

1—the N samples collected from the subsidiary branch (SB) according to the previous sampling method are used,
2—each of the N samples is precisely analyzed by a method other than Raman spectrometry, for example by chromatography,
3—the results of the stage 2 analysis are compared with those obtained by the Raman spectrometer so as to readjust the calibration coefficients for each of the constituents.

DETAILED DESCRIPTION OF THE INVENTION

1) Presentation of the Device According to the Invention

The present invention can be defined as a device for measuring concentration by analyzing a Raman spectrum relating to sampling points of a simulated moving bed xylenes separation unit (called an SMB unit). Said SMB separation unit is constituted by two adsorbers denoted A and B connected in series, i.e. there is a first recirculation stream connecting the bottom of adsorber B to the top of adsorber A and a second circulation stream connecting the bottom of adsorber A to the top of adsorber B.

The device according to the present invention is constituted by two identical and independent routes, called analysis route 1 (AR1) and analysis route 2 (AR2), each route having two branches, one called the main branch (denoted MB) operating for the majority of the time, the other called the subsidiary branch (denoted SB) operating for a minority of the time, and the sampling points being defined as follows:

for analysis route 1 (AR1)
   a) internal circulation current sent from adsorber B to adsorber A,
   b) extract originating from one or other of the adsorbers,
   c) raffinate originating from one or other of the adsorbers, for analysis route 2 (AR2)
   d) distilled raffinate (leaving distillation column C),
   e) internal circulation current from adsorber A to adsorber B,
   f) feed of the unit at the inlet of one or other of the adsorbers, each analysis route comprising two distinct branches with mutually exclusive operation, branch 1, called the "main" branch (MB) being used for the Raman analysis, and branch 2 called the called "subsidiary" branch (SB) being used for collecting samples, and branch 1 of each analysis route comprising the following main components taken in the direction of the stream to be analyzed:

a shut-off valve (1),
   a filter body (2) into which is inserted a filtering strainer with a cut-off threshold comprised between 3 and 15 microns and preferentially comprised between 5 and 7 micrometres,
   an exchanger (3) in which the hydrocarbon circulates on the tube side and cooling water on the shell side, comprising on the shell side a circulation of cooling water at a temperature comprised between 5° C. and 40° C., and on the tube side a circulation of hydrocarbons, the inlet temperature of which is comprised between 135° C. and 175° C. and the outlet temperature between 20° C. and 60° C.,
   a pressure regulator (15) making it possible to regulate the downstream pressure and a pressure measurement means such that based on an upstream pressure comprised between 0.9 and 1.6 MPa, a constant downstream pressure comprised between 0.2 and 0.5 MPa can be obtained, The circuit is separated into 2 parallel branches by means of a tee-fitting Branch No. 1, Called the Main Branch, for the Raman Analysis (and Denoted MB):

This main branch comprises the following components:
   A shut-off valve (6) making it possible to force the circulation into branch No. 2 (and to isolate the circulation cell),
   A local flowmeter (5) and a manual needle valve making it possible to regulate a flow rate between 5 and 60 l/h,
   a thermocouple (7),
   an analysis cell (8) with an internal volume of 1 cm$^3$, such that the liquid circulates between 2 sapphire windows,
   a pair of shut-off valves (9, 9') for isolating the analysis cell (8) in the event of maintenance,
   the 2 parallel branches being joined by means of a tee-fitting According to the safety regulations in force at the different sites, the assembly constituted by the optrode (10) and the analysis cell (8) is preferentially fitted in a containment system. In this case, there is moreover a flame arrester (not shown in FIG. 2) in branch No. 1 at the inlet and at the outlet of the circulation line in the system.

Branch No. 2, Called the "Subsidiary Branch", for Collecting Samples (and Denoted SB):

The circulation in branch No. 2 takes place in a highly exceptional manner (typically less than 1% of the operating time).

The subsidiary branch (SB) comprises the following components:
   a needle valve (11) making it possible to regulate the flow rate in the sampling branch,
   a 3-way 2-position pneumatic valve (12), the sampling position being directed to a needle valve making it possible to accurately adjust the quantity of sample collected to the volume of the available containers.
   a shut-off valve (13) making it possible to force the circulation into branch No. 1 (MB)
   a non-return valve (14) at the first analysis route (AR1) outlet, A tee-fitting makes it possible to join together the return lines of the two analysis routes to a point of lower pressure.

According to a preferred variant, the total volume of the circuit between the sampling point and the measuring point is such that the circulation time between the two points is comprised between 1 second and 75 seconds when the linear speed in the analysis cell (8) is comprised between 0.08 and 0.12 m/second.

In the simulated moving bed para-xylene separation unit, highly flammable liquids are generally handled at a high temperature and pressure. The equipment must therefore be in general explosion-proof, and comply with local regulations relating to equipment capable of coming into contact with explosive atmospheres; (for example, the ATEX regulation based on the European directives 94/9/CE or ATEX 137). In particular the power supplies are generally low voltage and the cables are protected by metal sheathing.

The equipment is generally dimensioned in order to maintain pressure and therefore either to be protected by safety valves calibrated in order to open well before the mechanical breakage of said equipment, or to maintain the maximum discharge pressure of the pumps.

The small-sized equipment intended to process the streams for analysis are generally protected by a locked metal cabinet. The optical fibres conveying the laser signal are generally contained in metal sheathing.

2) Choice of the Streams to be Analyzed:

As already stated, in normal operation analysis route 1 (AR1) processes the internal circulation current sent from adsorber B to adsorber A, and analysis route 2 (AR2) processes the distilled raffinate (leaving distillation column C).

Nevertheless under certain circumstances (start-up, malfunction situations etc.), it is possible to process other streams which are indicated below.

1.) The Feed to be Separated Containing Para-Xylene:

Most of the time (steady-state operation of the group of units constituting the aromatic complex) the feed to be separated in the SMB unit is of constant composition and depends only on the operating and working conditions of the units for catalytic reforming, transalkylation, and isomerization of the C8 aromatics.

Real-time continuous analysis is therefore not very useful.

Sampling once a day with a result supplied a few hours later is more than enough. However, during the transitional phases (starting, changes of feed at the inlet of the complex, change of operating conditions of one of the abovementioned units), this composition can vary fairly rapidly and, in this case, real-time continuous analysis of the feed makes it possible to anticipate the adjustments to be carried out on the simulated moving bed separation unit.

2.) The Internal Recirculation Current

In the SMB separation unit, a concentration chromatogram or profile is established, the feature of which is to move constantly around a loop constituted by the molecular sieve beds arranged in the adsorbers. This profile makes 1, 2 or 3 turns around the loop per hour. Inside the profile, variations of steep gradient and amplitude are observed in the concentrations in terms of constituents (on a scale of the order of a minute).

The shape of this concentration profile is, for a constant temperature and a given feed composition, only a function of the 4 internal liquid flow rates, and of the permutation time of the adsorbent solid beds.

The operator of the unit must be able to carry out 2 types of adjustments on a daily basis:
  increasing or reducing production in order to adapt to demand and
  adjusting the purity and yield as a function of the very small variations in temperature
  or the feed composition, or also the flow rate controllers' instrument drift.

The internal recirculation current must therefore, according to the invention, be constantly analyzed at at least one point, and in certain cases analyzed at 2 points. In normal operation, the recirculation current from the bottom of adsorber B to the top of adsorber A is analyzed by means of analysis route 1 (AR1).

3.) The Raffinate After Distillation (Feed of the Isomerization Unit Situated Downstream):

The continuous measurement of the residual para-xylene content of this stream gives the loss (or according to the difference, the yield) of the simulated moving bed separation unit. The accuracy of the analysis is sufficient for measuring the para-xylene contents generally comprised between 0.1% and 2% by weight, and preferably between 0.2% and 0.9% by weight.

This information in conjunction with that above makes it possible to adjust the unit on a daily basis. It is very difficult to measure the purity of the para-xylene after distillation. The Raman analyzer is generally not accurate enough for measuring traces of meta-xylene, ortho-xylene and ethylbenzene of the order of 0.04 to 0.1% by weight for each of these three compounds.

4.) The Extract and/or the Raffinate:

In the event of malfunction of the SMB separation unit, it can optionally be useful to measure the composition of the extract and/or of the raffinate directly leaving the molecular sieve beds in order to detect a fault linked to a particular bed.

The sampling process according to the present invention is characterized by the fact that the components of the device are calculated in order to simultaneously ensure:
1) coordination with the permutations of the N beds constituting the SMB separation unit,
2) a linear speed of the sample in the line comprised between 0.02 and 0.25 m/sec, and preferably between 0.05 and 0.2 m/sec, and very preferably between 0.08 and 0.12 m/sec.

3) Location of the Sampling Points:

The aim is to minimize the path between the sampling points and the optrode (10) on the one hand, and between the sampling points and the analyzed stream collecting points, on the other hand. This minimal path arrangement makes it possible to establish a rapid sampling loop.

The streams of the industrial process of separation by adsorption circulate at a fairly high temperature (from 140 to 210° C.) and pressure (from 0.1 MPa to 2 MPa relative) and in pipes with a diameter generally comprised between 0.1 to 0.5 m.

On the large pipe, a branch connection with a much smaller diameter (typically from 0.003 to 0.012 m) is made at a point chosen in order to have the highest available pressure.

For the first analysis route (AR1), the branch connection is preferably located between one of the recirculation pumps and an internal flow rate or recirculation pressure control valve.

The pressure-temperature pair is chosen as follows: 150° C. to 185° C., 1.6 to 2 MPa.

The maximum discharge pressure of the pump at zero flow rate: 4 MPa.

In the event of the simulated moving bed unit operating in degraded mode, the sampling line is disconnected from analysis route 1 (AR1) in order to connect it to one of the following 2 points:
  Extract leaving adsorber, just upstream of the extract control valve:
  The pressure-temperature pair is chosen as follows: pressure variable from 0.9 to 1.4 MPa, temperature in the range of from 150° C. to 185° C., Raffinate leaving adsorber: just upstream of the raffinate control valve:

The pressure-temperature pair is chosen as follows: pressure variable from 0.9 to 1.4 MPa, temperature within the range of from 150° C. to 185° C., For the second analysis route (AR2), 3 branch connections are made, each of them with a valve at the end and converging at a common point:

Distilled raffinate: located at the discharge of the feed pump of the isomerization unit, pressure-temperature pair chosen as follows: temperature of 120° C. to 160° C., pressure of 1 to 1.6 MPa, Feed: located between the discharge of the feed pump and the feed control valve, pressure-temperature pair chosen as follows: temperature of 150° C. to 185° C., pressure of 1.6 to 2 MPa, Recirculation Liquid Sent from the Bottom of Adsorber A to the Top of Adsorber B.

The pressure-temperature pair is chosen as follows: temperature comprised between 0° and 80° C., pressure comprised between 0.15 to 0.5 MPa relative.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding FR application No. 13/55.516, filed Jun. 14, 2013 are incorporated by reference herein.

EXAMPLES ACCORDING TO THE INVENTION

1) Example of Operation of an Analysis Route (AR1)

Filtration of Particles in Suspension (Common to the 2 Branches):

Separation of the para-xylene from the aromatic C8 cuts is carried out on an adsorbent solid, generally a zeolite of the faujasite family.

This solid is presented in the form of beads of a size generally comprised between 0.3 and 0.8 mm in diameter. These beads are themselves constituted by crystallites.

During the initial loading of the solid adsorbent into the unit, despite all the precautions being taken, crystallites become detached from the beads, for example by attrition or due to the drop height of the bead.

It is at the initial start of the period of adjustment of the unit that the concentration of crystallites in the internal recycling current and in the effluents (extract and raffinate) is highest. The stream to be analyzed should therefore be filtered in order to avoid distorting the optical measurement and fouling the parts of the device described below.

Filters having a cut-off threshold comprised between 3 and 15 micrometres are preferably used, which are changed regularly with a frequency varying from 6 hours when the adsorbers are started up to approximately one week when the adsorbers are in steady state operation.

Strainers made of sintered metal which have the advantage of being able to be reused after cleaning in an ultrasound bath.

Flow Rate and Speed of the Sample in Front of the Optrode (Branch No. 1):

This criterion is fixed by 2 considerations:

1.) maximum routing time between the sampling point and the analysis point equal to 75 seconds (corresponding to the permutation period of the solid beds), 2.) exposure time for each measurement in the spectrometer equal to one second.

The metal cabinet containing the analysis device is positioned as close as possible to the sampling point of the internal recirculation stream. The minimum diameter of the pipe welded onto the main pipeline for collecting the sample is between half an inch and 15 mm, with a flow section of approximately 1 cm$^2$, the length of this pipe is 5 metres, A reduction in diameter is then made in order to connect to the inlet valve of the metal cabinet containing the analyzer, starting from this valve a pipe with a diameter of 6 mm or quarter of an inch is used, with a flow section of approximately 0.125 cm$^2$. Given the components present in the analysis cabinet, the equivalent length to pipe of this section is 20 metres.

In order to meet the first of the 2 criteria of a time period of 75 seconds, there is a flow rate of 10 cm$^3$/second (50 seconds between the main pipeline and the inlet to the analysis cabinet and 25 seconds in the analysis device itself) i.e. a flow rate of 36 l/h.

The second criterion makes it possible to choose the volume of the cell to be placed opposite the optrode: for an analysis time of one second and a flow rate of 10 cm$^3$/sec, a volume of 1 cm$^3$ makes it possible to renew 10 times the volume, which allows thorough rinsing to be carried out.

Choice of the Temperature and the Cooling Surface of the Exchanger (3):

Cooling water at a temperature comprised between 5° C. and 40° C. is generally available, according to the different sites and the different seasons. In the worst case, (cooling water at 40° C. with a flow rate at least 10 times higher than that of the sample to be cooled), temperature of the sample to be analyzed of approximately 150° C. at the inlet to the analysis cabinet, maximum temperature of the sample of 60° C. in the containment system, a exchange surface of 0.2 m$^2$ is required given a transfer coefficient of 500 W/m$^2$/° C., i.e. 12.5 m pipe length with a diameter of 6 mm, for a coil with external circulation of water.

For sites where the winter temperature can drop well below 0° C. a frost protection device is required in order to prevent the shell part of the exchanger from bursting due to the frost.

Given the size of the cooling exchanger and the flow rates and temperature of the cooling water, the temperature of the sample at the analysis point is 15° C. to 60° C. This temperature is of course measured just before the analysis point, and taken into account for calculating the mixture compositions.

Choice of the Test Pressure of the Analysis Device:

The test pressure within the analysis device is calculated relative to the maximum discharge pressure values of the recirculation pump with a safety factor of 2, the circulation cell undergoes hydraulic testing at 8 MPa.

The working pressure of the device is equivalent to that of the pressure-relief valve of the vessel containing the solid adsorbent i.e. 1.9 MPa.

An expansion valve makes it possible to regulate the pressure downstream between 0.2 and 0.5 MPa.

Thus dimensioned and operated, analysis route AR1 of the device according to the invention makes it possible to carry out on-line analyses by RAMAN spectroscopy, either of the internal circulation current sent from adsorber B to adsorber A, or of the extract or the raffinate originating from one or other of the adsorbers.

2) Example of Operation of Branch (SB) of an Analysis Route

In addition to the Raman analysis, a series of analyses by gas chromatography is occasionally carried out.

This sampling is automated for a series of N+1 samples coordinated with the permutations of the N beds (N is the number of solid adsorbent beds).

The supervisor opens and closes a solenoid valve which sends compressed air to the pneumatic valve in order to direct the sample to a sample container. A typical sampling sequence is synchronized with the permutation of the adsorbent beds:

T=0 permutation of the 1st bed, the stream circulates in branch No. 2 of the Raman analysis cabinet, T=5 seconds opening for 5 sec. (abbreviation of second) to the external sampling: rinsing of the lines, T=10 sec closing for 5 sec. of sampling, the stream circulates in branch No. 2 of the Raman analysis cabinet, T=15 sec. opening for 10 sec. to the external sampling: collecting of 100 $cm^3$ by container No. 1, T=25 sec. closing, the stream circulates in branch No. 2 of the Raman analysis cabinet, T=75 sec. permutation of the 2nd bed, the stream circulates in branch No. 2 of the Raman analysis cabinet, T=80 sec. opening for 5 sec. to the external sampling: rinsing of the lines, T=85 sec. closing for 5 sec. of the sampling, T=90 sec. opening for 10 sec. to the external sampling: collecting of 100 $cm^3$ by container No. 2, T=100 sec. closing, the stream circulates in branch No. 2 of the Raman analysis cabinet This process is repeated successively for each of the beds in the loop. If there are 24 this leads to:

T=1725 sec. permutation of the 24th bed, the stream circulates in branch No. 2 of the Raman analysis cabinet, T=1730 sec. opening for 5 sec. to the external sampling: rinsing of the lines, T=1735 sec. closing for 5 sec. of the sampling, T=1740 sec. opening for 10 sec. to the external sampling: collecting of 100 $cm^3$ by container No. 24, T=1750 sec. closing, the stream circulates in branch No. 2 of the Raman analysis cabinet.

In order to verify that sampling has been carried out in a satisfactory manner, a sample is collected from the first bed (container No. 25 if there are 24 beds) for a second time; the 2 analyses should be identical.

Once this sampling has been completed, normal conditions of circulation in the analysis route are re-established (passing through branch No. 1 of the circuit).

When all the results of chromatography analysis of the 25 samples are available (generally approximately 24 hours after the samples have been collected), in addition to the measurement of the constituents present in the form of traces (non-aromatic constituents with 8 and 9 carbon atoms, and aromatic constituents with 9 and 10 carbon atoms) it is possible to compare, for toluene, the three xylenes (ortho-, meta-, para-), ethylbenzene and paradiethylbenzene, the values obtained by Raman spectroscopy just before and just after this sampling. This makes it possible to detect any drift of the results making a new calibration of the Raman spectrometer necessary.

The thus calibrated on-line analyses by Raman spectroscopy make it possible, by using for example all or part of the RAMAN analysis method described in U.S. Pat. No. 8,194,245, to continuously monitor the operation of the adsorbers by means of the device according to the invention and to detect any malfunction with a very small time lag.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A simulated moving bed xylenes separation system comprising:
   two adsorbers A and B connected in series, a first circulation line for the flow of a circulation stream originating from the bottom of adsorber A to the top of adsorber B, second circulation line for the flow of a circulation stream originating from the bottom of adsorber B to the top of adsorber A, each of said adsorbers having a feed inlet for introducing a feed stream, an extract outlet for removing an extract stream, and a raffinate outlet for removing a raffinate stream;
   a distillation column C for distilling raffinate; and
   a device for measuring concentration by analyzing a Raman spectrum relating to sampling points, said device having two independent analysis routes, called analysis route 1 and analysis route 2, each of said analysis routes having a main branch operating for a majority of the time and a subsidiary branch operating for a minority of the time,
   wherein for analysis route 1 the streams that can be sampled are
      a) circulation stream sent from adsorber B to adsorber A,
      b) extract originating from one or other of adsorbers A and B,
      c) raffinate originating from one or other of adsorbers A and B,
   wherein for analysis route 2 the fluids that can be sampled are
      d) distilled raffinate leaving distillation column C,
      e) circulation stream from adsorber A to adsorber B,
      f) feed of the unit at the inlet of one or other of adsorbers A and B,
   wherein in each of said analysis routes said main branch and said subsidiary branch exhibit mutually exclusive operation, and the main branch of each of said analysis routes is used for the Raman analysis, and the subsidiary branch of each said analysis routes is used for sample collection, and said main branch of each analysis route comprises the following main components taken in the direction of the stream to be analyzed:
   a shut-off valve (6) making it possible to force the circulation into said subsidiary branch in certain situations,
   a thermocouple (7) making it possible to take the temperature of the sample to be analyzed,
   an analysis cell (8) containing an optrode (10), receiving an input laser signal and sending an output signal to the Raman spectrometer, the internal volume of said measurement cell being of the order of 1 $cm^3$, and
   a second shut-off valve (9) for isolating the analysis cell in the event of maintenance.

2. The simulated moving bed xylenes separation system according to claim 1, wherein said analysis cell (8) and the optrode (10) are both contained in a containment cell.

3. The simulated moving bed xylenes separation system according to claim 1, wherein said optrode (10) is linked to an input optical fiber providing a laser signal at a wavelength between 400 and 1080 nm.

4. The simulated moving bed xylenes separation system according to claim 1, wherein for the majority of the time:
analysis route 1 is connected to the second circulation line for the circulation stream passing from adsorber B to adsorber A,
analysis route 2 is connected to a line removing distilled raffinate originating from distillation column C.

5. The simulated moving bed xylenes separation unit according to claim 4, wherein, in the event of maintenance on the analysis route 1, the analysis route 2 is connected to the first circulation line for the circulation stream passing from adsorber A to adsorber B.

6. The simulated moving bed xylenes separation unit according to claim 4, wherein the sampling point and the point at which the concentration is measured by analyzing a Raman spectrum are positioned such that the circulation time between said sampling point and said point at which the concentration is measured is between 1 and 75 seconds, the linear speed in the analysis cell (8) being comprised between 0.02 and 0.25 m/s.

7. A method for analyzing concentrations in a simulated moving bed xylenes separation system according to claim 1, comprising analyzing concentrations using said device for measuring concentration by analyzing a Raman spectrum, wherein said analysis cell (8) of said device operates under the following conditions:
1) the sample contains less than 10 ppb of slid particles in suspension,
2) the sample temperature is between 20° C. and 60° C.,
3) the sample pressure is between 0.2 and 0.5 MPa,
4) the linear speed is between 0.02 and 0.25 m/sec.

8. A method for the analysis of concentrations in a simulated moving bed xylenes separation system according to claim 1, comprising analyzing concentrations using said device for measuring concentration by analyzing a Raman spectrum, wherein when the simulated moving bed is operating in degraded mode, the sampling line is disconnected from analysis route 1 and connected to at one of the following points:
a line for removal of extract from an adsorber, just upstream of an extract control valve:
the pressure-temperature pair being chosen as follows: pressure variable from 0.9 to 1.4 MPa, temperature in the range from 150° C. to 185° C.; and
a line for removal of raffinate from an adsorber, just upstream of a raffinate control valve:
the pressure-temperature pair being chosen as follows: pressure variable from 0.9 to 1.4 MPa, temperature comprised between 150° C. and 185° C.

9. A method for the analysis of concentrations in a simulated moving bed xylenes separation system according to claim 1, comprising analyzing concentrations using said device for measuring concentration by analyzing a Raman spectrum, wherein said analysis route 2 is applied to one of the following sampling points:
Distilled raffinate: located at the discharge of a feed pump of an isomerization unit, temperature comprised between 120° C. to 160° C., pressure comprised between 1 to 1.6 MPa,
Feed: located between the discharge of a feed pump and a feed control valve, temperature comprised between 150° C. and 185° C., pressure comprised between 1.6 to 2 MPa,
circulation stream sent from the bottom of adsorber A to the top of adsorber B, temperature comprised between 0° and 80° C., pressure comprised between 0.15 to 0.5 MPa relative.

* * * * *